United States Patent
Uchiumi et al.

(10) Patent No.: US 10,765,401 B2
(45) Date of Patent: Sep. 8, 2020

(54) ULTRASONIC DIAGNOSTIC DEVICE

(71) Applicant: Toshiba Medical Systems Corporation, Otawara-shi (JP)

(72) Inventors: Isao Uchiumi, Nasushiobara (JP); Nobuyuki Iwama, Nasushiobara (JP); Yasuo Miyajima, Utsunomiya (JP); Hironobu Hongou, Otawara (JP); Takatoshi Okumura, Yaita (JP); Koichi Morikawa, Nasushiobara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 725 days.

(21) Appl. No.: 14/736,386

(22) Filed: Jun. 11, 2015

(65) Prior Publication Data

US 2015/0359511 A1 Dec. 17, 2015

(30) Foreign Application Priority Data

Jun. 12, 2014 (JP) ................................. 2014-121752

(51) Int. Cl.
*A61B 8/00* (2006.01)
*A61B 8/14* (2006.01)
*A61B 8/08* (2006.01)

(52) U.S. Cl.
CPC .............. *A61B 8/14* (2013.01); *A61B 8/5207* (2013.01); *A61B 8/54* (2013.01); *A61B 8/4444* (2013.01)

(58) Field of Classification Search
CPC ............ A61B 8/14; A61B 8/5207; A61B 8/54
See application file for complete search history.

(56) References Cited

U.S. PATENT DOCUMENTS

| | | | | |
|---|---|---|---|---|
| 5,353,798 | A | * 10/1994 | Sieben | A61B 8/12 128/925 |
| 2004/0002658 | A1 | 1/2004 | Marian, Jr. | |
| 2012/0197122 | A1* | 8/2012 | Kurt | A61B 8/467 600/440 |
| 2014/0142436 | A1* | 5/2014 | Hutchins | A61B 5/0035 600/478 |

FOREIGN PATENT DOCUMENTS

| | | |
|---|---|---|
| JP | 63-3618 A | 1/1988 |
| JP | 2005-278665 A | 10/2005 |

OTHER PUBLICATIONS

Office Action dated Jan. 30, 2018 in corresponding Japanese Patent Application No. 2014-121752.

* cited by examiner

*Primary Examiner* — Joseph M Santos Rodriguez
(74) *Attorney, Agent, or Firm* — Oblon, McClelland, Maier & Neustadt, L.L.P.

(57) ABSTRACT

An ultrasonic diagnostic device according to an embodiment includes an ultrasonic probe and transformer circuitry. The ultrasonic probe transmits ultrasonic waves to a subject and converts reflection waves reflected by the subject to a reflection wave signal. The transformer circuitry includes an auto transformer that transforms the reflection wave signal at a transformation ratio in accordance with a control signal based on information related to the ultrasonic probe among a plurality of transformation ratios.

7 Claims, 5 Drawing Sheets

FIG.3
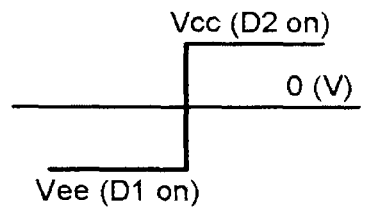
FIG.4
| PROBE ID | CONTROL SIGNAL LEVEL |
|---|---|
| AA | NEGATIVE |
| AB | POSITIVE |
| ⋮ | ⋮ |
FIG.5
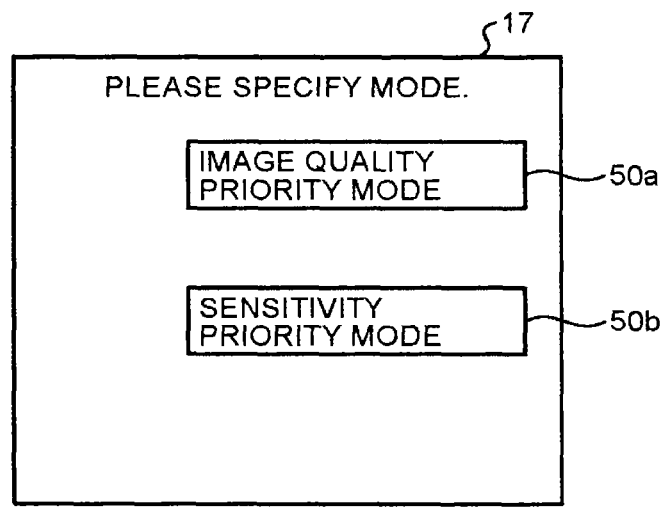

ULTRASONIC DIAGNOSTIC DEVICE

CROSS-REFERENCE TO RELATED APPLICATION

This application is based upon and claims the benefit of priority from Japanese Patent Application No. 2014-121752, filed on Jun. 12, 2014 the entire contents of all of which are incorporated herein by reference.

FIELD

Embodiments described herein relate generally to an ultrasonic diagnostic device.

BACKGROUND

Conventionally, there are ultrasonic diagnostic devices that transmit ultrasonic waves to a subject, receive reflection waves reflected by tissues in the subject, image a reception signal (reflection wave signal) based on the received reflection waves, and display the imaged reception signal.

For example, in the conventional ultrasonic diagnostic devices, a transformer in which a primary coil and a secondary coil are separated boosts the reception signal at a predetermined boosting ratio so as to make receiving sensitivity preferable. It should be noted that the receiving sensitivity is also expressed by noise figure (NF) in some cases.

In the above-mentioned conventional ultrasonic diagnostic devices, large leakage inductance is generated on the transformer in which the primary coil and the secondary coil are separated in some cases. When the large leakage inductance is generated on the transformer, high-frequency characteristics are deteriorated in some cases. For example, a high-frequency band is limited in some cases. When the high-frequency characteristics are deteriorated, receiving sensitivity is deteriorated in some cases.

BRIEF DESCRIPTION OF THE DRAWINGS

FIG. 3 is a diagram illustrating an example of a control signal that is input to the transformer circuitry;

FIG. 4 is a table for explaining a first modification of the first embodiment;

FIG. 5 is a diagram for explaining a second modification of the first embodiment;

DETAILED DESCRIPTION

An ultrasonic diagnostic device according to an embodiment includes an ultrasonic probe and transformer circuitry. The ultrasonic probe transmits ultrasonic waves to a subject and converts reflection waves reflected by the subject to a reflection wave signal. The transformer circuitry includes an auto transformer that transforms the reflection wave signal at a transformation ratio in accordance with a control signal based on information related to the ultrasonic probe among a plurality of transformation ratios.

Hereinafter, embodiments of the ultrasonic diagnostic device will be described in detail with reference to the accompanying drawings.

First Embodiment

Figure 1:
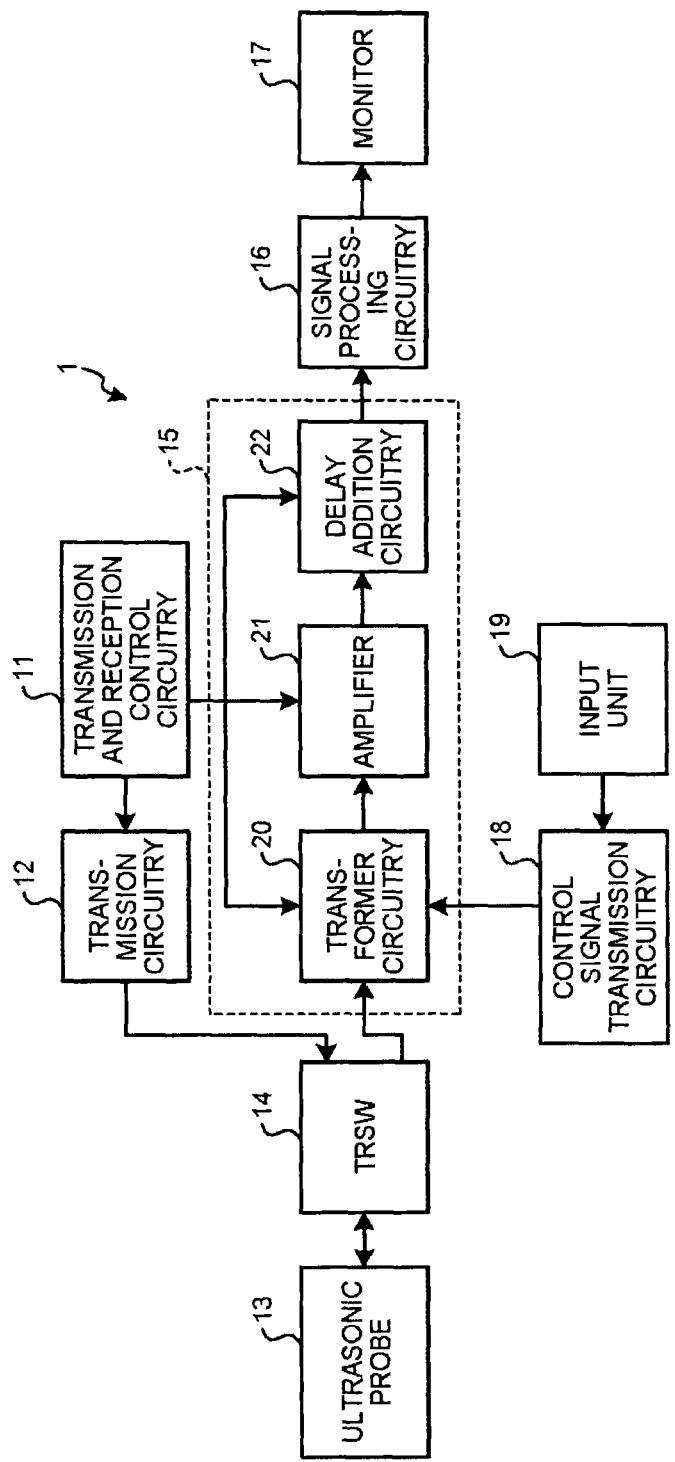
FIG. 1 is a diagram illustrating an example of the configuration of an ultrasonic diagnostic device according to a first embodiment.

First, the configuration of an ultrasonic diagnostic device according to a first embodiment is described. FIG. 1 is a diagram illustrating an example of the configuration of the ultrasonic diagnostic device in the first embodiment.

Example of Configuration of Ultrasonic Diagnostic Device

As illustrated in FIG. 1, an ultrasonic diagnostic device 1 includes transmission and reception control circuitry 11, transmission circuitry 12, an ultrasonic probe 13, a transmission and reception chance-over switch (TRSW) 14, reception circuitry 15, signal processing circuitry 16, a monitor 17, control signal transmission circuitry 18, and an input unit 19.

The transmission and reception control circuitry 11 is connected to the transmission circuitry 12 and the reception circuitry 15. The transmission and reception control circuitry 11 is a processor having a function of controlling the transmission circuitry 12 and the reception circuitry 15 so as to cause the transmission circuitry 12 and the reception circuitry 15 to perform operations, which will be described later. The transmission and reception control circuitry 11 reads a program corresponding to this function from storage circuitry (not illustrated) storing therein the program and executes the read program so as to execute the function corresponding to the program.

The transmission circuitry 12 is connected to the TRSW 14. The transmission circuitry 12 receives control by the transmission and reception control circuitry 11 and supplies a transmission signal (high-voltage pulse waves) to transducer elements (not illustrated), which will be described later, that are incorporated in the ultrasonic probe 13. For example, the transmission circuitry 12 supplies the transmission signal to the transducer elements, which will be described later, through the TRSW 14. For example, the transmission signal normally has a large amplitude of approximately 100 Vpp for driving the transducer elements of the ultrasonic probe 13, which will be described later.

The ultrasonic probe 13 includes a plurality of transducer elements having a plurality of transducers that transmit ultrasonic waves to the subject and receive reflection waves reflected by tissues in the subject. It should be noted that the transducer elements are arranged in a two-dimensional array form, for example.

The ultrasonic probe 13 is connected to the TRSW 14. When the transmission signal from the transmission circuitry 12 is input to the ultrasonic probe 13 through the TRSW 14, the transducer elements of the ultrasonic probe 13 transmit the ultrasonic waves in accordance with the transmission signal to the subject. The transducer elements receive the reflection waves reflected in the subject and convert the received reflection waves to electric signals. The transducer elements transmit the electric signals to the TRSW 14 as reception signals. Note that the reception signal is also referred to as a reflection wave signal.

The TRSW 14 is connected to the reception circuitry 15. The TRSW 14 transmits the transmission signal transmitted from the transmission circuitry 12 to the transducer elements. The TRSW 14 transmits the reception signals transmitted from the ultrasonic probe 13 to the reception circuitry 15.

The reception circuitry 15 is provided for each reception channel. Each reception circuitry 15 includes transformer circuitry 20, an amplifier 21, and delay addition circuitry 22. It should be noted that the reception circuitries 15 the number of which is the same as the number of reception channels are provided but only one reception circuitry 15 is illustrated in FIG. 1 for the convenience of explanation and description is also made for one reception circuitry 15 below. The number of reception channels is the same as the number of transducer elements, which will be described later. As another example, a configuration in which the numbers of transmission and reception channels are set to be smaller than the number of transducer elements and connection to all the transducer elements can be made by combining an analog switch and switching the transmission and reception channels may be employed.

The transformer circuitry 20 is connected to the transmission and reception control circuitry 11, the TRSW 14, the control signal transmission circuitry 18, and the amplifier 21. The transformer circuitry 20 transforms the reception signal transmitted from the TRSW 14 at a transformation ratio corresponding to a control signal, which will be described later, transmitted from the control signal transmission circuitry 18. Then, the transformer circuitry 20 transmits the transformed reception signal to the amplifier 21.

The amplifier 21 is connected to the transmission and reception control circuitry 11 and the delay addition circuitry 22. The amplifier 21 amplifies the reception signal transmitted from the transformer circuitry 20 at a predetermined amplification factor. The amplifier 21 transmits the amplified reception signal to the delay addition circuitry 22. For example, the amplifier 21 is a preamplifier that amplifies the reception signal at a predetermined amplification factor.

The delay addition circuitry 22 is connected to the transmission and reception control circuitry 11 and the signal processing circuitry 16. The delay addition circuitry 22 performs well-known delay addition processing of applying delay to the reception signal transmitted from the amplifier 21 and adding the reception signal such that the reception signal has appropriate directivity. For example, the delay addition circuitry 22 performs analog-to-digital (A/D) conversion processing of converting the reception signal as an analog signal to a digital signal on the reception signal, and performs the delay addition processing on the reception signal converted to the digital signal. Then, the delay addition circuitry 22 transmits the reception signal on which the delay addition processing has been performed to the signal processing circuitry 16.

The signal processing circuitry 16 is connected to the monitor 17. The signal processing circuitry 16 performs well-known pieces of signal processing of various types on the reception signal transmitted from the delay addition circuitry 22 so as to generate a reception signal indicating an ultrasonic image. Then, the signal processing circuitry 16 transmits the generated reception signal indicating the ultrasonic image to the monitor 17.

When the monitor 17 receives the reception signal transmitted from the signal processing circuitry 16, the monitor 17 displays the ultrasonic image indicated by the received reception signal.

The control signal transmission circuitry 18 is connected to the input unit 19. The control signal transmission circuitry 18 generates a control signal for controlling the transformer circuitry 20 to transform the reception signal at a transformation ratio specified by a user and received by the input unit 19. The control signal transmission circuitry 18 transmits the generated control signal to the transformer circuitry 20. For example, the control signal transmission circuitry 18 is a processor having the above-mentioned function. The control signal transmission circuitry 18 reads a program corresponding to the above-mentioned function from storage circuitry (not illustrated) storing therein the program and executes the read program so as to execute the function corresponding to the program.

The input unit 19 is configured by a mouse, a keyboard, a trackball, a touch panel, a switch button, a remote control, a tablet terminal, a microphone, a Kinect, or the like receiving, from the user, the transformation ratio specified by the user when the transformer circuitry 20 transforms the reception signal. The input unit 19 transmits an electric signal indicating the transformation ratio received from the user to the control signal transmission circuitry 18. The user specifies any one of transformation ratios at which the transformer circuitry 20 can transform the reception signal. When the input unit 19 is configured by a tablet terminal and the tablet terminal receives the transformation ratio from the user, the tablet terminal transmits an electric signal indicating the received transformation ratio to the control signal transmission circuitry 18 by wired communication or wireless communication. When the input unit 19 is configured by a microphone and the microphone receives an audio signal indicating the transformation ratio from the user, the microphone converts the received audio signal to an electric signal indicating the transformation ratio and transmits the electric signal indicating the transformation ratio to the control signal transmission circuitry 18. When the input unit 19 is configured by a Kinect, the Kinect recognizes a gesture of the user, specifies a transformation ratio indicated by the gesture of the user, and transmits an electric signal indicating the specified transformation ratio to the control signal transmission circuitry 18.

The expression "processor" used in the description above indicates, for example, a central preprocess unit (CPU), a graphics processing unit (GPU), or circuitry such as an application specific integrated circuit (ASIC) and a programmable logic device (for example, a simple programmable logic device (SPLD), a complex programmable logic device (CPLD), and a field programmable gate array (FPGA)).

Furthermore, the above-mentioned storage circuitry is configured by a semiconductor memory element such as a random access memory (RAM) and a flash memory, a hard disk, an optical disk, or the like.

Figure 2:
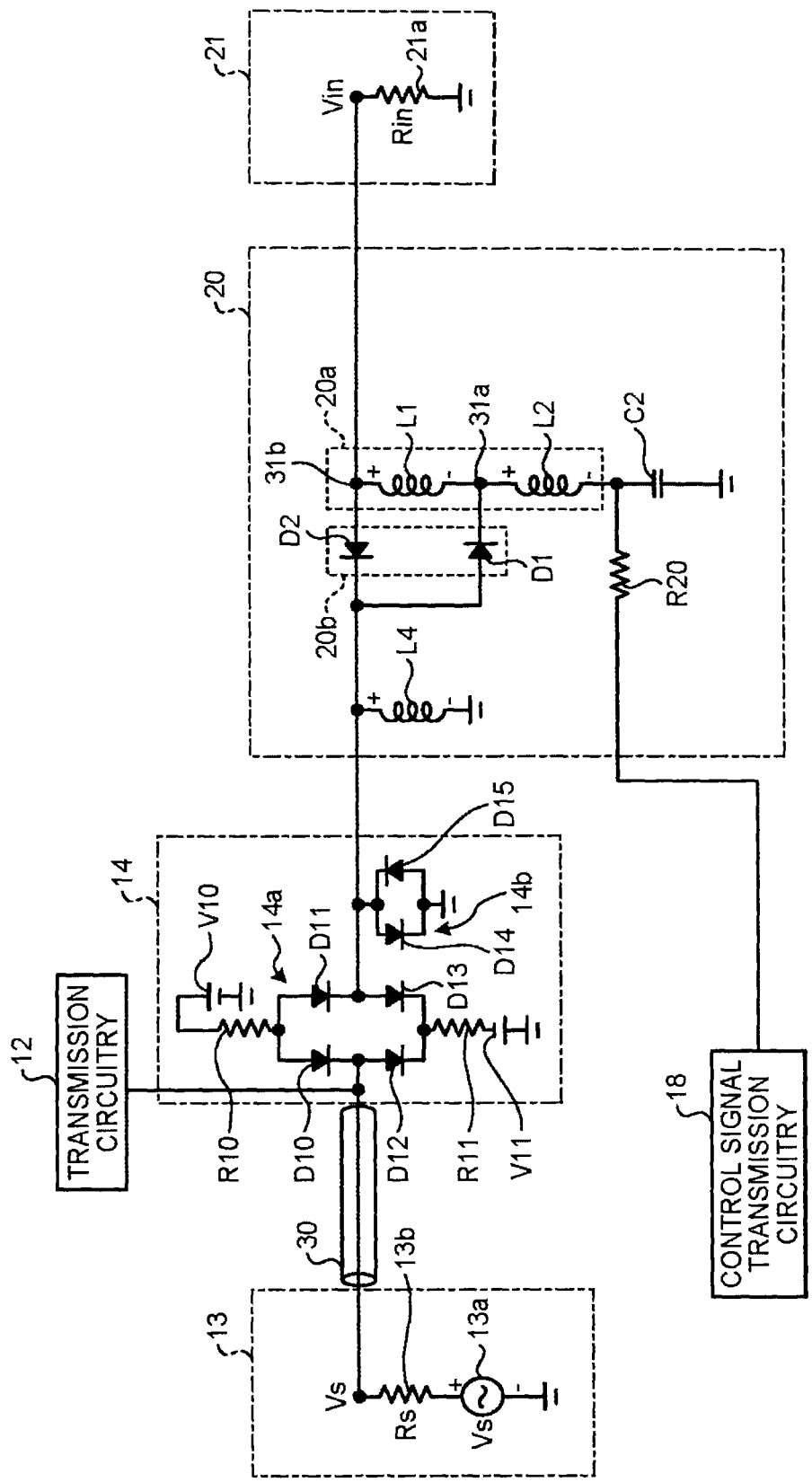
FIG. 2 is a diagram for explaining specific examples of the configurations of a transmission and reception changeover switch (TRSW) and transformer circuitry as illustrated in FIG. 1.

Next, specific examples of the configurations of the TRSW 14 and the transformer circuitry 20 will be described. FIG. 2 is a diagram for explaining the specific examples of the configurations of the TRSW 14 and the transformer circuitry 20 as illustrated in FIG. 1.

In an example of FIG. 2, equivalent circuits of the ultrasonic probe 13 and the amplifier 21 are also illustrated. As illustrated in the example of FIG. 2, the ultrasonic probe 13 is equivalent to a circuit in which a resistor 13b corresponding to signal source impedance (internal impedance) Rs is connected to a signal source 13a that outputs a reception signal of a voltage Vs. As illustrated in the example of FIG. 2, the amplifier 21 is equivalent to a circuit including a resistor 21a corresponding to input impedance Rin of the amplifier 21. As illustrated in FIG. 2, the ultrasonic probe 13 and the TRSW 14 are connected with a cable 30.

The TRSW 14 includes diode bridge circuitry 14a and clamping circuitry 14b. The diode bridge circuitry 14a includes bias power sources V10 and V11, a bias resistor R10 that is connected to the bias power source V10, a bias resistor R11 that is connected to the bias power source V11, and diodes D10 to D13. The clamping circuitry 14b includes diodes D14 and D15 to which polarities different from each other are connected. The clamping circuitry 14b is grounded. In the example of FIG. 2, the diode D14 is a diode an anode of which is connected to a transmission path through which the reception signal flows and a cathode of which is grounded. The diode D15 is a diode a cathode of which is connected to the transmission path through which the reception signal flows and an anode of which is grounded.

In transmission, inputs of the transformer circuitry 20 and the amplifier 21 are protected from a high-voltage pulse of a transmission signal with an amplitude limiting function of the TRSW 14 configured by combining the diode bridge circuitry 14a and the clamping circuitry 14b.

By contrast, as in the case where the amplitude is small (for example, smaller than several 100 mVpp) like the reception signal, the reception signal is weaker than a bias current flowing through the bias resistor R10, the diodes D10 to D13, and the bias resistor R11 of the diode bridge circuitry 14a and the diodes D10 to D13 are not therefore turned OFF. That is, the reception signal passes through the diodes D10 to D13 as it is. The reception signal that has passed is input to the transformer circuitry 20. For example, when a forward voltage Vf of the diodes D14 and D15 is 0.7 V, a voltage of the reception signal that is input to the transformer circuitry 20 is limited to approximately 1.4 Vpp at maximum.

As illustrated in FIG. 2, the transformer circuitry 20 includes a tap-equipped auto transformer 20a (hereinafter, referred to as auto transformer 20a), a change-over switch 20b, a coil L4, a capacitor C2, and a bias resistor R20.

The auto transformer 20a includes a coil L1 and a coil L2. The coil L1 and the coil L2 are connected in series. For example, one end of the coil L1 is connected to one end of the coil L2. The other end of the coil L1 is connected to the transmission path through which the reception signal flows. The other end of the coil L2 is connected to the capacitor C2 and the bias resistor R20.

The auto transformer 20a includes a tap 31a provided between one end of the coil L1 and one end of the coil L2. The auto transformer 20a further includes a tap 31b provided at the other end side of the coil L1.

The magnitude of leakage inductance that is generated on the auto transformer 20a is smaller than the magnitude of leakage inductance that is generated on a transformer in which the primary coil and the secondary coil are separated. That is, the leakage inductance is generated between the coils L1 and L2 in FIG. 2 only when boosting is made with the coils L1 and L2. By contrast, the coils L1 and L2 are only connected in parallel with the amplifier 21 when boosting is not made and it is considered that the leakage inductance is not present on a system transmitting the reception signal in the equivalent circuit. As a result, the auto transformer 20a can reduce an influence by the leakage inductance in comparison with the transformer in which the primary coil and the secondary coil are separated. The auto transformer 20a therefore prevents deterioration in the high-frequency characteristics. Accordingly, the embodiment can prevent deterioration in the receiving sensitivity.

The auto transformer 20a is smaller in size than the transformer in which the primary coil and the secondary coil are separated. The auto transformer 20a is cheaper than the transformer in which the primary coil and the secondary coil are separated. Accordingly, the embodiment can reduce the reception circuitry 15 in size and cost.

The change-over switch 20b includes diode switches D1 and D2. An anode of the diode switch D1 is connected to the coil L4 and a cathode thereof is connected to the tap 31a. An anode of the diode switch D2 is connected to the tap 31b and a cathode thereof is connected to the coil L4. The diode switch D1 or the diode switch D2 of the change-over switch 20b is turned ON in accordance with the polarity of a bias current, which will be described later. That is to say, the change-over switch 20b switches whether the reflection wave signal is boosted by the transformer circuitry 20.

In the embodiment, the change-over switch 20b is provided at the input side of the auto transformer 20a. This is because parasitic capacitance is increased and the high-frequency characteristics are deteriorated if the change-over switch 20b is provided at the output side of the auto transformer 20a. The presence of the parasitic capacitance at the output side of the auto transformer 20a lowers the input impedance Rin of the amplifier 21 to "1/boosting ratio"-fold. Furthermore, an influence of the impedance by the parasitic capacitance also becomes "1/boosting ratio"-fold in the same manner. The change-over switch 20b is provided at the input side of the auto transformer 20a in the embodiment in order to prevent deterioration in performance of the high-frequency probe expecting a boosting effect by the auto transformer 20a because the impedance by the parasitic capacitance is lowered at a high frequency.

The above-mentioned diode switches D1 and D2 that are used for the change-over switch 20b have low parasitic capacitances, thereby preventing deterioration in the high-frequency characteristics. It should be noted that a field effect transistor (FET) or a transistor can be also used instead of the diode switches D1 and D2.

The coil L4 is a coil causing the bias current for turning ON the diode switches D1 and D2 to flow. One end of the coil L4 is grounded and the other end thereof is connected to the anode of the diode switch D1 and the cathode of the diode switch D2. For example, a coil having a large inductance value so as not to serve as an attenuation element for the reception signal is used as the coil L4.

One end of the capacitor C2 is connected to the other end of the coil L2 and the other end of the capacitor C2 is grounded.

One end of the bias resistor R20 is connected to the other end of the coil L2 and the other end of the bias resistor R20 is connected to the control signal transmission circuitry 18. It should be noted that an input terminal to which the control signal is input is provided between the bias resistor R20 and the control signal transmission circuitry 18.

Next, operations of the transformer circuitry 20 will be described. FIG. 3 is a diagram illustrating an example of the control signal that is input to the transformer circuitry 20. As illustrated in FIG. 3, a voltage of the control signal is negative when the diode switch D1 is turned ON whereas a voltage of the control signal is positive when the diode switch D2 is turned ON. In the following description, the signal of which "voltage is negative" is expressed as a "negative signal" and the signal of which "voltage is positive" is expressed as a "positive signal".

For example, when the reception signal is not boosted (when the boosting ratio specified by the user is "1"), the control signal transmission circuitry 18 transmits the positive signal to the transformer circuitry 20 as the control signal. When the positive signal is input to the transformer circuitry 20, that is, when the positive voltage is applied to the input terminal, bias current flows through the bias resistor R20, the coil L2, the coil L1, the diode switch D2, and the coil L4. The diode switch D2 is turned ON by the bias current. When the diode switch D2 is turned ON, the reception signal is applied to the coil L1 and the coil L2 and is boosted at a boosting ratio "(number of windings of the coil L1+number of windings of the coil L2)/(number of windings of the coil L1+number of windings of the coil L2)"="1". Then, the reception signal boosted at the boosting ratio "1" is transmitted to the amplifier 21. That is to say, when the positive signal is input to the transformer circuitry 20, the reception signal is transmitted to the amplifier 21 as it is. The reception signal being not boosted means the same as the reception signal being boosted at the boosting ratio "1". The boosting ratio is an example of a transformation ratio.

By contrast, when the reception signal is boosted at a boosting ratio higher than 1 (for example, the boosting ratio specified by the user is "(number of windings of the coil L1+number of windings of the coil L2)/(number of windings of the coil L2)"), the control signal transmission circuitry 18 transmits the negative signal to the transformer circuitry 20 as the control signal. When the negative signal is input to the transformer circuitry 20, that is, when the negative voltage is applied to the input terminal, bias current flows through the coil L4, the diode switch D1, the coil L2, and the bias resistor R20. The diode switch D1 is turned ON by the bias current. When the diode switch D1 is turned ON, the reception signal is applied to the coil L2 and is boosted at a boosting ratio "(number of windings of the coil L1+number of windings of the coil L2)/(number of windings of the coil L2)". Then, the reception signal boosted at the boosting ratio "(number of windings of the coil L1+number of windings of the coil L2)/(number of windings of the coil L2)" is transmitted to the amplifier 21. That is to say, when the negative signal is input to the transformer circuitry 20, the reception signal is boosted at a boosting ratio higher than 1 and is transmitted to the amplifier 21.

An example of a reason why the reception signal is boosted before being input to the amplifier 21 is described. For example, when the reception signal is boosted at a boosting ratio "1" (that is to say, when the reception signal is input to the amplifier 21 as it is), input-referred noise Enin as total noise that is input to the amplifier 21 is expressed by the following equation (1) under an assumption that thermal noise on the signal source 13a is Vn and input-referred voltage noise on the amplifier 21 is En. It should be noted that in the following equation, In (input-referred current noise) of the amplifier is omitted for simplification of explanation.

$$Enin=(Vn^2+En^2)^{1/2} \quad (1)$$

NF (unit: dB) when the reception signal is boosted at a boosting ratio "1" is expressed by the following equation (2).

$$NF=20\times\log[(vn^2+En^2)^{1/2}/Vn] \quad (2)$$

When the reception signal is boosted at a boosting ratio "K", input-referred noise Enin as total noise that is input to the amplifier 21 is expressed by the following equation (3).

$$Enin=((K\times Vn)^2+En^2)^{1/2} \quad (3)$$

NF when the reception signal is boosted at the boosting ratio "K" is expressed by the following equation (4).

$$NF=20\times\log[((K\times Vn)^2+En^2)^{1/2}/(K\times Vn)] \quad (4)$$

As a value of NF is closer to 0, receiving sensitivity is more preferable. As a value of Vn is smaller than a value of En, the value of NF is larger, as indicated by the equation (2). As the value of NF is larger, the receiving sensitivity is deteriorated. By contrast, as indicated by the equation (4), when the boosting ratio "K" is larger than 1 and the reception signal is boosted at the boosting ratio "K", the value of NF is closer to 0 relative to the case where the boosting ratio is "1" and the receiving sensitivity is improved to be preferable. In order to make the value of NF close to 0 so as to make the receiving sensitivity preferable, the transformer circuitry 20 in the embodiment boosts the reception signal. Practically, the boosting by the transformer has limitations to improve the receiving sensitivity due to influence of the input-referred current noise In.

When the ultrasonic probe 13 is a probe capable of handling a frequency of lower than 7 MHz, for example, what is called low-frequency probe, signal source impedance Rs is not so large relative to that in the case of a high-frequency probe. The value of Vn is increased in proportion to the magnitude of the signal source impedance Rs. When the ultrasonic probe 13 is the low-frequency probe, it is highly possible that the value of Vn is not so large relative to the value of En. In this case, large improvement in the receiving sensitivity is not observed.

By contrast, when the ultrasonic probe 13 is a probe capable of handling a frequency of equal to or higher than 7 MHz, for example, what is called the high-frequency probe, the signal source impedance Rs is larger than that in the case of the low-frequency probe. When the ultrasonic probe 13 is the high-frequency probe, it is highly possible that the value of Vn is larger than the value of En. Accordingly, when the ultrasonic probe 13 is the high-frequency probe, the reception signal is boosted at a high boosting ratio. When the ultrasonic probe 13 is the low-frequency probe, it is sufficient that the reception signal is boosted at a boosting ratio lower than that in the case of the high-frequency probe or the reception signal input to the transformer circuitry 20 is transmitted to the amplifier 21 as it is.

The ultrasonic diagnostic device 1 in the first embodiment has been described above. As described above, the ultrasonic diagnostic device 1 transforms the reception signal at a boosting ratio in accordance with the control signal based on information related to the ultrasonic probe 13 among a plurality of boosting ratios using the auto transformer 20a having low leakage inductance. The ultrasonic diagnostic device 1 therefore prevents deterioration in the high-frequency characteristics. Accordingly, the ultrasonic diagnostic device 1 can prevent deterioration in the receiving sensitivity.

As described above, according to the embodiment, the reception signal is transformed using the auto transformer 20a reduced in size and cost, thereby reducing the reception circuitry 15 in size and cost.

Furthermore, the ultrasonic diagnostic device 1 in the first embodiment prevents deterioration in the high-frequency characteristics. The ultrasonic diagnostic device 1 can therefore provide an ultrasonic image of which image quality is prevented from being deteriorated even when the ultrasonic probe 13 is the high-frequency probe.

The input impedance Rin of the amplifier 21 changes in proportion to the square of the boosting ratio. Accordingly, it is preferable that the input impedance Rin be switched in accordance with the boosting ratio. For example, a well-known amplifier capable of switching the input impedance is preferably used as the amplifier 21.

Although the auto transformer 20a boosts the reception signal at the boosting ratio in accordance with the control signal in the description above, the operation that is performed by the auto transformer 20a is not limited thereto. For example, the auto transformer 20a can step down the reception signal at a step-down ratio in accordance with the control signal with the same principle. For example, when the input-referred noise Enin is dominant, the auto transformer 20a can step down the reception signal so as to increase the thermal noise Vn on the signal source 13a and improve the receiving sensitivity. It should be noted that the step-down ratio is an example of the transformation ratio.

Although the ultrasonic diagnostic device 1 includes the signal processing circuitry 16 and the monitor 17 in the description above, the ultrasonic diagnostic device 1 may not include the monitor 17. The ultrasonic diagnostic device 1 may not include the monitor 17 and the signal processing circuitry 16. Alternatively, the ultrasonic diagnostic device 1 may not include the monitor 17 and a part of the signal processing circuitry 16.

First Modification of First Embodiment

In the above-mentioned first embodiment, the control signal transmission circuitry 18 transmits the control signal corresponding to the boosting ratio specified by the user to the transformer circuitry 20. Alternatively, the control signal transmission circuitry 18 may transmit the control signal in accordance with the signal source impedance of the ultrasonic probe 13 that is used for the ultrasonic diagnostic device 1 to the transformer circuitry 20. Such an embodiment is described with reference to FIG. 4 as a first modification of the first embodiment.

FIG. 4 is a diagram for explaining the first modification of the first embodiment. In the first modification, storage circuitry provided at the inside or the outside of the control signal transmission circuitry 18 stores therein a table 40 as illustrated in FIG. 4. The storage circuitry is configured by a semiconductor element such as a RAM and a flash memory, a hard disk, an optical disk, or the like. The table 40 has items of a "probe ID" and a "control signal level".

A probe ID as identification (ID) of an ultrasonic probe capable of being used as the ultrasonic probe 13 is registered in the item of the "probe ID". When signal source impedance of the ultrasonic probe indicated by the probe ID registered in the item of the "probe ID" of the same record is larger than a predetermined threshold, "negative" indicating that the control signal to be transmitted to the transformer circuitry 20 is a negative signal is registered in the item of the "control signal level". When the control signal that is transmitted to the transformer circuitry 20 is the negative signal, the reception signal is boosted. When the signal source impedance of the ultrasonic probe indicated by the probe ID registered in the item of the "probe ID" of the same record is equal to or smaller than the predetermined threshold, "positive" indicating that the control signal to be transmitted to the transformer circuitry 20 is a positive signal is registered in the item of the "control signal level". When the control signal that is transmitted to the transformer circuitry 20 is the positive signal, the reception signal input to the transformer circuitry 20 is transmitted to the amplifier 21 as it is.

In the first modification, the control signal transmission circuitry 18 specifies a probe ID of the ultrasonic probe 13 (ultrasonic probe 13 connected to the TRSW 14) that is used for the ultrasonic diagnostic device 1. An example of a method of specifying the probe ID is described. For example, the control signal transmission circuitry 18 is connected to the ultrasonic probe 13 through the cable 30 and acquires the probe ID from the ultrasonic probe 13 so as to specify the probe ID. Then, the control signal transmission circuitry 18 acquires the control signal level corresponding to the specified probe ID from the table 40. When the control signal transmission circuitry 18 acquires "negative", the control signal transmission circuitry 18 transmits the negative signal to the transformer circuitry 20 as the control signal. When the control signal transmission circuitry 18 acquires "positive", the control signal transmission circuitry 18 transmits the positive signal to the transformer circuitry 20 as the control signal.

The ultrasonic diagnostic device 1 in the first modification of the first embodiment has been described above. As described above, the ultrasonic diagnostic device 1 in the first modification transmits the control signal corresponding to the boosting ratio appropriate for the signal source impedance of the ultrasonic probe 13 to the transformer circuitry 20. For example, when it is preferable that the reception signal be boosted at a boosting ratio higher than 1, the ultrasonic diagnostic device 1 transmits the control signal corresponding to the boosting ratio higher than 1 to the transformer circuitry 20. When it is preferable that the reception signal be transmitted to the transformer circuitry 20 as it is, the ultrasonic diagnostic device 1 transmits the control signal corresponding to the boosting ratio "1" to the transformer circuitry 20. Accordingly, the ultrasonic diagnostic device 1 in the first modification can prevent deterioration in the receiving sensitivity without requiring the user to specify the boosting ratio.

Second Modification of First Embodiment

The control signal transmission circuitry 18 may transmit, to the transformer circuitry 20, a control signal in accordance with a mode specified by a user from a mode in which the receiving sensitivity is prioritized and a mode in which image quality of the ultrasonic image is prioritized. Such an embodiment is described with reference to FIG. 5 as a second modification of the first embodiment.

FIG. 5 is a diagram for explaining the second modification of the first embodiment. In the second modification, the input unit 19 is connected to the monitor 17. As illustrated in an example of FIG. 5, the input unit 19 causes a message "please specify a mode" for prompting the user to specify any mode of the mode in which the receiving sensitivity is prioritized and the mode in which the image quality of the ultrasonic image is prioritized and buttons 50a and 50b capable of being pressed by the user to be displayed on the monitor 17. The button 50a is a button enabling the user to specify the mode in which the image quality is prioritized. The button 50b is a button enabling the user to specify the mode in which the receiving sensitivity is prioritized. When the button 50a is pressed, the input unit 19 notifies the control signal transmission circuitry 18 of specification of the mode in which the image quality is prioritized. By contrast, when the button 50b is pressed, the input unit 19 notifies the control signal transmission circuitry 18 of specification of the mode in which the receiving sensitivity is prioritized.

When the control signal transmission circuitry 18 is notified of the specification of the mode in which the receiving sensitivity is prioritized, the control signal transmission circuitry 18 performs pieces of processing the same as those in the above-mentioned first embodiment until the mode in which the receiving sensitivity is prioritized is cancelled. That is to say, when the reception signal is not boosted (when the boosting ratio specified by the user is "1"), the control signal transmission circuitry 18 transmits the positive signal to the transformer circuitry 20 as the control signal. When the reception signal is boosted at a boosting ratio higher than 1 (for example, the boosting ratio specified by the user is "(number of windings of the coil L1+number of windings of the coil L2)/(number of windings of the coil L2)"), the control signal transmission circuitry 18 transmits the negative signal to the transformer circuitry 20 as the control signal.

By contrast, when the control signal transmission circuitry 18 is notified of the specification of the mode in which the image quality is prioritized, the control signal transmission circuitry 18 transmits the control signal corresponding to the boosting ratio "1" to the transformer circuitry 20 until the mode in which the image quality is prioritized is cancelled. The reception signal input to the transformer circuitry 20 is transmitted to the amplifier 21 as it is, so that generation of saturation on the amplifier 21 is prevented. This prevention of generation of saturation makes image quality of the ultrasonic image preferable.

The ultrasonic diagnostic device 1 in the second modification of the first embodiment has been described above. As described above, the ultrasonic diagnostic device 1 in the second modification transmits a signal for boosting the reception signal at the boosting ratio "1" to the transformer circuitry 20 as the control signal when the mode in which the image quality of the ultrasonic image based on the reception signal is prioritized is specified. That is to say, the ultrasonic diagnostic device 1 in the second modification transmits a signal for outputting the reception signal as it is without boosting as the control signal to the transformer circuitry 20. Accordingly, the ultrasonic diagnostic device 1 in the second modification can make the image quality of the ultrasonic image based on the reception signal preferable when the mode in which the image quality of the ultrasonic image is prioritized.

Second Embodiment

Next, an ultrasonic diagnostic device according to a second embodiment will be described. It should be noted that the same reference numerals denote the same configurations as those in the first embodiment and description thereof is omitted in some cases. An ultrasonic diagnostic device according to the second embodiment is different from the ultrasonic diagnostic device 1 in the first embodiment in that the ultrasonic diagnostic device in the second embodiment includes transformer circuitry 60 different from the transformer circuitry 20.

Figure 6:
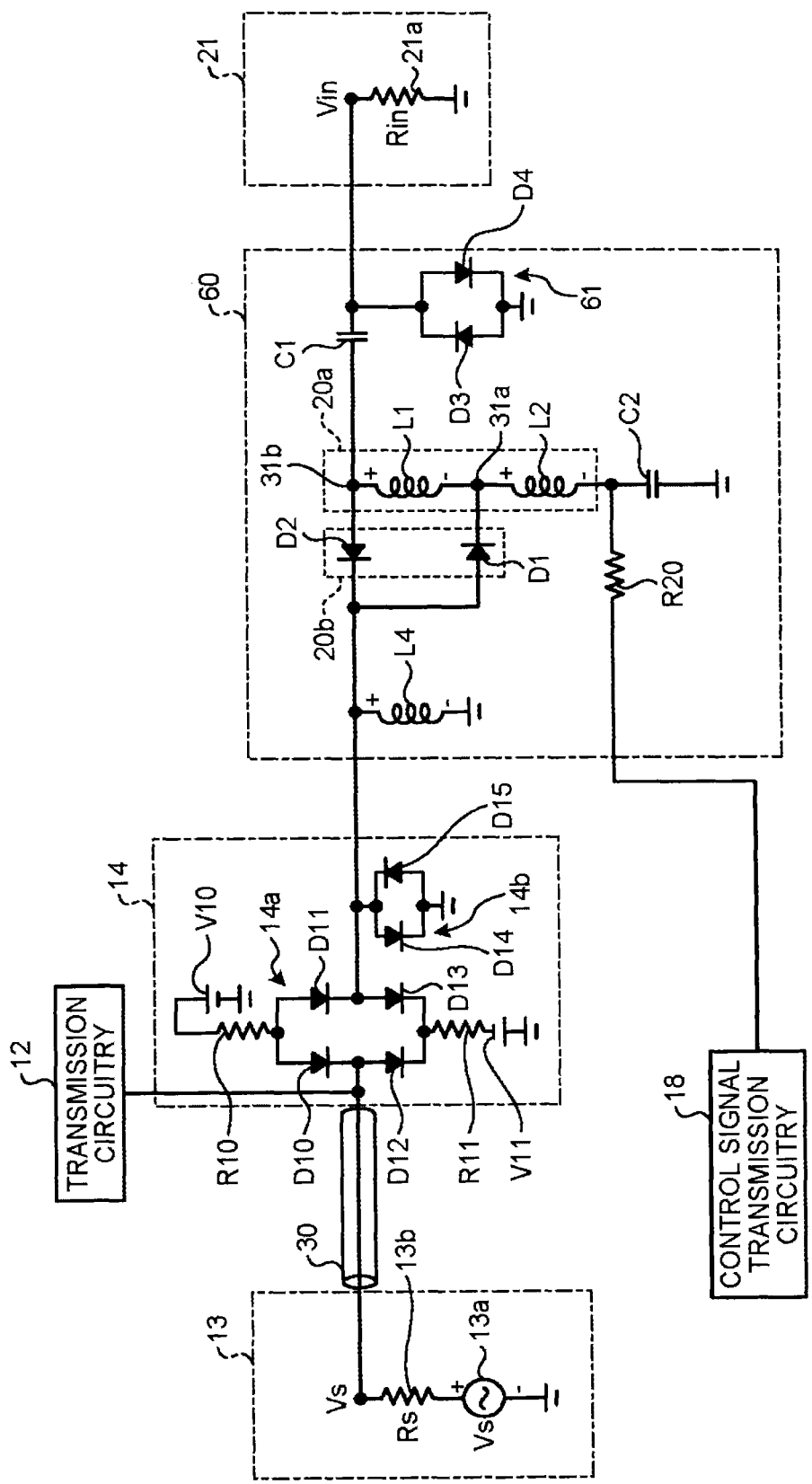
FIG. 6 is a diagram illustrating an example of the configuration of transformer circuitry according to a second embodiment.

FIG. 6 is a diagram illustrating an example of the configuration of the transformer circuitry in the second embodiment. As illustrated in FIG. 6, the transformer circuitry 60 in the second embodiment includes a capacitor C1 and limiter circuitry 61 in addition to the configuration of the transformer circuitry 20.

The limiter circuitry 61 includes diodes D3 and D4 to which polarities different from each other are connected. The limiter circuitry 61 is grounded. In the example of FIG. 6, the diode D3 is a diode a cathode of which is connected to the transmission path through which the reception signal flows and an anode of which is grounded. The diode D4 is a diode an anode of which is connected to the transmission path through which the reception signal flows and a cathode of which is grounded. The limiter circuitry 61 has an amplitude limiting function and limits the amplitude of the reception signal that is input to the amplifier 21 in accordance with a value of a forward voltage Vf of the diodes D3 and D4. For example, when the forward voltage Vf of the diodes D3 and D4 is 0.7 V, a voltage of the reception signal that is input to the amplifier 21 is limited to approximately 1.4 Vpp at maximum. With this limitation, the reception signal boosted by the auto transformer 20a is input to the amplifier 21 as it is, and generation of saturation on the amplifier 21 can be prevented. Furthermore, increase in recovery time from the saturation can be prevented on the amplifier 21.

Only by providing the limiter circuitry 61 at a subsequent stage of the auto transformer 20a, positive and negative symmetry of the reception signal that is input to the amplifier 21 is lost due to the forward voltage Vf of the diodes D3 and D4. For example, the reception signal shifts to the negative side. The lost in the positive and negative symmetry occurs because when the bias current flows through the coil L4, a voltage is generated by voltage drop due to small series resistance that the coil L4 has and a direct-current (DC) voltage is generated on the limiter circuitry 61. In order to make the positive and negative symmetry of the reception signal preferable, in the second embodiment, the capacitor C1 is provided at a previous stage of the limiter circuitry 61. The capacitor C1 is connected to the auto transformer 20a and the limiter circuitry 61 by alternating-current (AC) coupling. That is to say, the capacitor C1 is provided at a position on the transmission path through which the reception signal flows, closer to the transformer circuitry 20 relative to a position at which the limiter circuitry 61 is connected to the transmission path through which the reception signal flows. The capacitor C1 has a function of preventing a DC voltage from being generated on the limiter circuitry 61, thereby making the positive and negative symmetry of the reception signal passing through the limiter circuitry 61 preferable.

The second embodiment has been described above. According to the second embodiment, the limiter circuitry 61 has the amplitude limiting function so as to prevent generation of saturation on the amplifier 21. Furthermore, increase in the recovery time from the saturation can be prevented on the amplifier 21.

Furthermore, according to the second embodiment, the capacitor C1 is provided at the previous stage of the limiter circuitry 61. The provision of the capacitor C1 enables the positive and negative symmetry of the reception signal passing through the limiter circuitry 61 to be made preferable, thereby making the positive and negative symmetry of the reception signal that is input to the amplifier 21 preferable.

The second embodiment can provide the same effects as those of the ultrasonic diagnostic device 1 in the first embodiment.

Third Embodiment

In the first embodiment, there are two transformation ratios when the reception signal is transformed. Alternatively, equal to or more than three transformation ratios when the reception signal is transformed may be set. An embodiment in which there are three transformation ratios when the reception signal is transformed is described with reference to FIG. 7 as a third embodiment. It should be noted that the same reference numerals denote the same configurations as those in the first embodiment and the second embodiment and description thereof is omitted in some cases. An ultrasonic diagnostic device according to the third embodiment is different from the ultrasonic diagnostic device 1 in the first embodiment in that the ultrasonic diagnostic device in the third embodiment includes transformer circuitry 70 different from the transformer circuitry 20.

Figure 7:
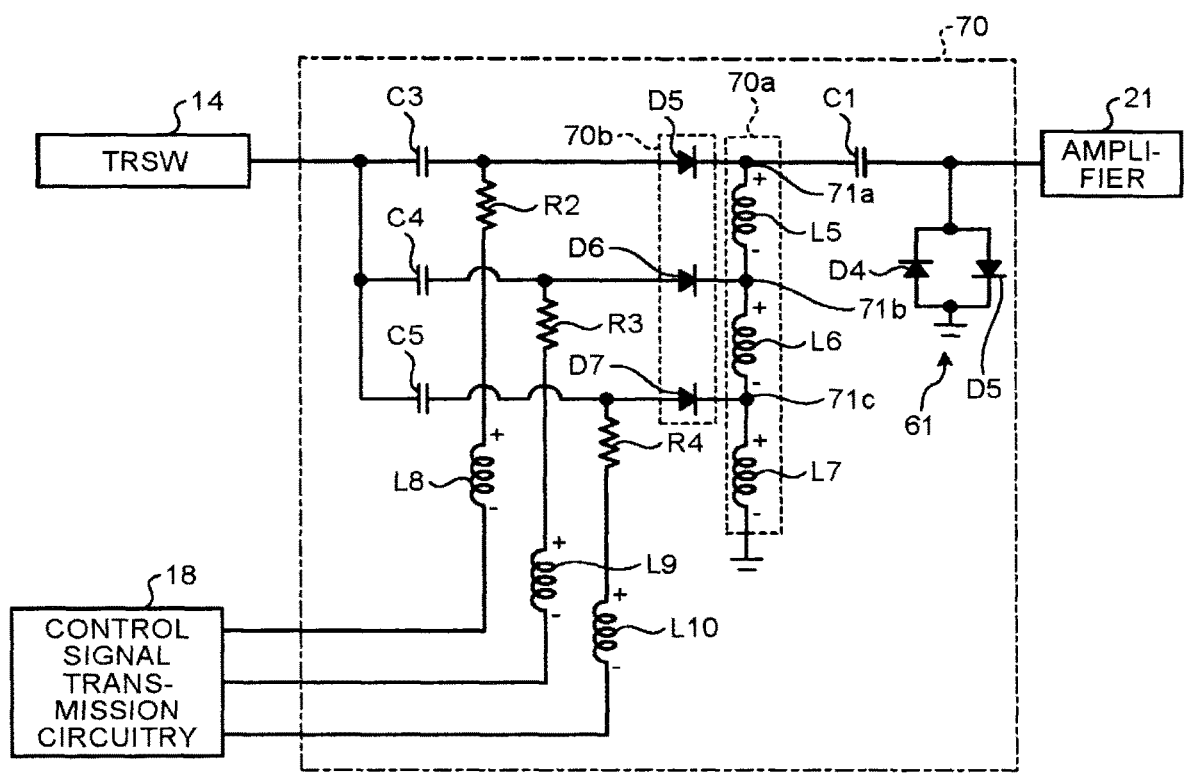
FIG. 7 is a diagram illustrating an example of the configuration of transformer circuitry according to a third embodiment.

FIG. 7 is a diagram illustrating an example of the configuration of the transformer circuitry in the third embodiment. As illustrated in FIG. 7, the transformer circuitry 70 in the third embodiment includes a tap-equipped auto transformer 70a (hereinafter, referred to as auto transformer 70a), a change-over switch 70b, coils L8 to L10, capacitors C3 to C5, bias resistors R2 to R4, the limiter circuitry 61, and the capacitor C1.

The auto transformer 70a includes coils L5 to L7. The coil L5, the coil L6, and the coil L7 are connected in series. For example, one end of the coil L5 is connected to one end of the coil L6. The other end of the coil L6 is connected to one end of the coil L7. The other end of the coil L5 is connected to the transmission path through which the reception signal flows. The other end of the coil L7 is grounded.

The auto transformer 70a includes a tap 71b provided between one end of the coil L5 and one end of the coil L6 and a tap 71c provided between the other end of the coil L6 and one end of the coil L7. The auto transformer 70a further includes a tap 71a provided at the other end side of the coil L5.

The magnitude of leakage inductance that is generated on the auto transformer 70a is smaller than the magnitude of leakage inductance that is generated on the transformer in which the primary coil and the secondary coil are separated for the following reason. That is, the leakage inductance is generated between the coils L5 and L6 and between the coils L6 and L7 only when boosting is made with the coil L5, the coil L6, and the coil L7 in FIG. 7. By contrast, the coils L5, L6, and L7 are only connected in parallel with the amplifier 21 when boosting is not made and it is considered that the leakage inductance is not present on a system transmitting the reception signal in the equivalent circuit. As a result, the auto transformer 70a can reduce influence by the leakage inductance in comparison with a normal transformer in which the primary coil and the secondary coil are separated. The auto transformer 70a therefore prevents deterioration in the high-frequency characteristics. Accordingly, the embodiment can prevent deterioration in the receiving sensitivity.

The auto transformer 70a is smaller in size than the transformer in which the primary coil and the secondary coil are separated. The auto transformer 70a is cheaper than the transformer in which the primary coil and the secondary coil are separated. Accordingly, the embodiment can achieve reduction in size and cost.

The change-over switch 70b includes diode switches D5 to D7. An anode of the diode switch D5 is connected to the capacitor C3 and the bias resistor R2 and a cathode thereof is connected to the tap 71a. An anode of the diode switch D6 is connected to the capacitor C4 and the bias resistor R3 and a cathode thereof is connected to the tap 71b. An anode of the diode switch D7 is connected to the capacitor C5 and the bias resistor R4 and a cathode thereof is connected to the tap 71c. The change-over switch 70b turns ON the diode switch D5, the diode switch D6, or the diode switch D7 in accordance with the polarity of the bias current.

One end of the bias resistor R2 is connected to the anode of the diode switch D5 and the other end of the bias resistor R2 is connected to the coil L8. One end of the bias resistor R3 is connected to the anode of the diode switch D6 and the other end of the bias resistor R3 is connected to the coil L9.

One end of the bias resistor R4 is connected to the anode of the diode switch D7 and the other end of the bias resistor R4 is connected to the coil L10.

One end of the capacitor C3 is connected to the TRSW 14 and the other end of the capacitor C3 is connected to the anode of the diode switch D5. One end of the capacitor C4 is connected to the TRSW 14 and the other end of the capacitor C4 is connected to the anode of the diode switch D6. One end of the capacitor C5 is connected to the TRSW 14 and the other end of the capacitor C5 is connected to the anode of the diode switch D7.

The coils L8 to L10 are coils causing the bias current for turning ON the diode switches D5 to D7 to flow. One end of the coil L8 is connected to the other end of the bias resistor R2 and the other end of the coil L8 is connected to the control signal transmission circuitry 18. One end of the coil L9 is connected to the other end of the bias resistor R3 and the other end of the coil L9 is connected to the control signal transmission circuitry 18. One end of the coil L10 is connected to the other end of the bias resistor R4 and the other end of the coil L10 is connected to the control signal transmission circuitry 18. An input terminal (first input terminal) to which the control signal is input is provided between the coil L8 and the control signal transmission circuitry 18. An input terminal (second input terminal) to which the control signal is input is provided between the coil L9 and the control signal transmission circuitry 18. Furthermore, an input terminal (third input terminal) to which the control signal is input is provided between the coil L10 and the control signal transmission circuitry 18.

Next, operations of the transformer circuitry 70 will be described. For example, when the user specifies the boosting ratio "1" (first boosting ratio), the control signal transmission circuitry 18 inputs the positive signal to the first input terminal as the control signal and inputs the negative signal to the second input terminal and the third input terminal as the control signal. When the positive signal is input to the first input terminal and the negative signal is input to the second input terminal and the third input terminal (that is, when the positive voltage is applied to the first input terminal and the negative voltage is input to the second input terminal and the third input terminal), the bias current flows through the coil L8, the bias resistor R2, the diode switch D5, and the coils L5 to L7. The diode switch D5 is turned ON by the bias current. When the diode switch D5 is turned ON, the reception signal is applied to the coils L5 to L7 and is boosted at a boosting ratio "(number of windings of the coil L5+number of windings of the coil L6+number of windings of the coil L7)/(number of windings of the coil L5+number of windings of the coil L6+number of windings of the coil L7)"="1". Then, the reception signal boosted at the boosting ratio "1" is transmitted to the amplifier 21. That is to say, the reception signal is transmitted to the amplifier 21 as it is.

When the user specifies the boosting ratio "(number of windings of the coil L5+number of windings of the coil L6+number of windings of the coil L7)/(number of windings of the coil L6+number of windings of the coil L7)" (second boosting ratio), the control signal transmission circuitry 18 inputs the positive signal to the second input terminal as the control signal and inputs the negative signal to the first input terminal and the third input terminal as the control signal. When the positive signal is input to the second input terminal and the negative signal is input to the first input terminal and the third input terminal (that is to say, when the positive voltage is applied to the second input terminal and the negative voltage is applied to the first input terminal and the third input terminal), the bias current flows through the coil L9, the bias resistor R3, the diode switch D6, and the coils L6 and L7. The diode switch D6 is turned ON by the bias current. When the diode switch D6 is turned ON, the reception signal is applied to the coils L6 and L7 and is boosted at a second boosting ratio. Then, the boosted reception signal is transmitted to the amplifier 21.

When the user specifies a boosting ratio "(number of windings of the coil L5+number of windings of the coil L6+number of windings of the coil L7)/(number of windings of the coil L7" (third boosting ratio), the control signal transmission circuitry 18 inputs the positive signal to the third input terminal as the control signal and inputs the negative signal to the first input terminal and the second input terminal as the control signal. When the positive signal is input to the third input terminal and the negative signal is input to the first input terminal and the second input terminal (that is to say, when the positive voltage is applied to the third input terminal and the negative voltage is applied to the first input terminal and the second input terminal), the bias current flows through the coil L10, the bias resistor R4, the diode switch D7, and the coil L7. The diode switch D7 is turned ON by the bias current. When the diode switch D7 is turned ON, the reception signal is applied to the coil L7 and is boosted at a third boosting ratio. Then, the boosted reception signal is transmitted to the amplifier 21.

The third embodiment has been described above. As described above, in the third embodiment, the reception signal is transformed at a boosting ratio in accordance with the control signal based on information related to the ultrasonic probe among a plurality of boosting ratios using the auto transformer 70a having low leakage inductance. The third embodiment therefore prevents deterioration in the high-frequency characteristics. Accordingly, the third embodiment can prevent deterioration in the receiving sensitivity.

As described above, according to the third embodiment, the reception signal is transformed using the auto transformer 70a reduced in size and cost, thereby achieving reduction in size and cost.

Furthermore, the third embodiment can provide the same effects as those in the first embodiment and the second embodiment.

In the third embodiment, there are three transformation ratios when the reception signal is transformed. Alternatively, the ultrasonic diagnostic device may transform the reception signal at any transformation ratio in accordance with the control signal among equal to or more than four transformation ratios in the same manner.

The ultrasonic diagnostic device according to at least one of the above-mentioned embodiments can prevent deterioration in the receiving sensitivity.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnostic device, comprising:
   an ultrasonic probe configured to transmit ultrasonic waves to a subject and convert reflection waves reflected by the subject to a reflection wave signal;
   transformer circuitry including an auto transformer configured to transform the reflection wave signal into a transformed reflection wave signal at a transformation ratio, which is determined in accordance with a control signal determined based on information related to the ultrasonic probe among a plurality of transformation ratios;
   control signal transmission circuitry configured to transmit, to the transformer circuitry, the control signal, which is determined in accordance with a frequency which the ultrasonic probe is capable of handling; and
   a switch provided at an input of the transformer circuitry, the switch being configured to switch whether the reflection wave signal is boosted by the transformer circuitry.

2. The ultrasonic diagnostic device according to claim 1, further comprising limiter circuitry configured to limit a magnitude of an amplitude of the reflection wave signal transformed by the transformer circuitry.

3. The ultrasonic diagnostic device according to claim 2, wherein
   the limiter circuitry includes a first diode a cathode of which is connected to a transmission path through which the reflection wave signal flows and an anode of which is grounded and a second diode an anode of which is connected to the transmission path through which the reflection wave signal flows and a cathode of which is grounded, and
   the transformer circuitry includes a capacitor provided at a position on the transmission path closer to the transformer circuitry relative to a position at which the first diode and the second diode are connected to the transmission path.

4. The ultrasonic diagnostic device according to claim 1, wherein the control signal transmission circuitry transmits a signal for outputting the reflection wave signal without transforming the reflection wave signal as the control signal to the transformer circuitry, when a mode is specified in which image quality of an image based on the reflection wave signal is prioritized.

5. The ultrasonic diagnostic device according to claim 2, wherein the control signal transmission circuitry transmits a signal for outputting the reflection wave signal without transforming the reflection wave signal as the control signal to the transformer circuitry, when a mode is specified in which image quality of an image based on the reflection wave signal is prioritized.

6. The ultrasonic diagnostic device according to claim 3, wherein the control signal transmission circuitry transmits a signal for outputting the reflection wave signal without transforming the reflection wave signal as the control signal to the transformer circuitry, when a mode is specified in which image quality of an image based on the reflection wave signal is prioritized.

7. The ultrasonic diagnostic device according to claim 1, wherein the ultrasonic probe is a high-frequency probe and the frequency that the ultrasonic probe is configured to handle is equal to or higher than 7 MHz.

* * * * *